United States Patent

Nishimura

[11] Patent Number: 5,137,028
[45] Date of Patent: Aug. 11, 1992

[54] CLINICAL THERMOMETER FOR WOMEN

[75] Inventor: Kinji Nishimura, Watarai, Japan

[73] Assignee: Nishimoto, Co., Ltd., Misono, Japan

[21] Appl. No.: 598,125

[22] Filed: Oct. 16, 1990

[30] Foreign Application Priority Data

Oct. 18, 1989 [JP] Japan ................................. 1-271222

[51] Int. Cl.⁵ ............................................. A61B 10/00
[52] U.S. Cl. ................................................. 128/738
[58] Field of Search ................. 128/736, 738; 374/170

[56] References Cited

U.S. PATENT DOCUMENTS

| | | | |
|---|---|---|---|
| 4,151,831 | 5/1979 | Lester | 128/738 |
| 4,377,171 | 3/1983 | Wada | 128/738 |
| 4,488,560 | 12/1984 | Takamura | 128/738 |
| 4,530,366 | 7/1985 | Nessi et al. | 128/738 |
| 4,771,791 | 9/1988 | Kubouchi | 128/738 |

FOREIGN PATENT DOCUMENTS

| | | |
|---|---|---|
| 0168640 | 6/1985 | European Pat. Off. . |
| 3606249 | 2/1986 | Fed. Rep. of Germany . |
| 2092340 | 12/1981 | United Kingdom . |

Primary Examiner—Max Hindenburg
Attorney, Agent, or Firm—Owen, Wickersham & Erickson

[57] ABSTRACT

A clinical thermometer for women having processing function to determine day of ovulation accurately and also having function to memorize the data for several menstruation periods and to display the data when desired to guide exact diagnosis.

9 Claims, 2 Drawing Sheets

CLINICAL THERMOMETER FOR WOMEN

BACKGROUND OF THE INVENTION

1. Field of the Invention

The present invention relates to a clinical thermometer for women that provides accurate measurement of a woman's basal body temperature and also produces data relating to birth control based on the measured basal body temperature.

2. Prior Art Statement

There are several clinical thermometer heretofore known which are especially adapted for women's use for measuring the basal body temperature for a certain required period and to calculate ovulation day based on the data relating to the measured basal body temperature and to indicate conceivable term being several days before and after the ovulation day.

The known women's clinical thermometer is a type to memorize the basal body temperature measured for a predetermined period, and to indicate the basal body temperature for each day unit on a display provided in the thermometer. However, it has a disadvantage in that a gynaecologist may take a little bit longer time to check the each day unit basal body temperature successively and to advise the patient accurately for birth control condition and that is difficult to exactly judge a changing date between the high temperature term and low temperature term and the ovulation day.

There are other known devices. But then operating principle or temperature detecting algorithm for the measurement of basal body temperature is rather simple. For instance, the thermometer is arranged just to memorize measured temperature immediately after a certain time lapse from the starting of the measurement of the body temperature and to take this value as the basal body temperature. Further known devices use the algorithm of an ordinary electronic thermometer, in which a search rate temperature is previously determined from the temperature increasing curve and such a temperature is judged as the basal body temperature. Accordingly, the conventional women's clinical thermometer has a big disadvantage in that the measured basal body temperature itself is not accurate.

The present applicant has filed Japanese patent applications in this respect as follows.

(1) Feb. 6, 1989 Application No. 26976/89
 Woman's thermometer with memory functions.
(2) Mar. 27, 1989 Application No. 74702/89
 Woman's thermometer with function of calculating area of corpus luteum.
(3) May 22, 1989 Application No. 128484/89
 Woman's thermometer with indicating function for birth control.
(4) Jul. 24, 1989 Application No. 191,201/89
 Woman's thermometer.

Each of the above four applications relates to a thermometer for rather particular use.

SUMMARY OF THE INVENTION

The present invention has for its object to solve the above mentioned problems of the prior art devices. In the present invention, an arrangement has been made to provide a device for a woman is accurately measuring basal body temperature, for printing out the total birth control data related to and based on the basal body temperature measured and memorized for a certain period of time, and for indicating the data by digital values or graphs so that the gynaecologist can make diagnosis properly.

In order to achieve the above mentioned object, the present invention is characterized in that it comprises
 calendar function means,
 detecting means for detecting body temperature of a woman to be supervised by using a temperature detector,
 temperature measuring means for supplying at its input a signal from said body temperature detecting means to recognize the detected body temperature and to judge basal body temperature under condition that variation of detected body temperature for a predetermined period is within a previously set permissible temperature range after judging the detected temperature had exceeded a predetermined temperature or the time lapsed from the starting the measurement of the body temperature had exceeded by a highest detected temperature during said predetermined period,
 body temperature memory means for memorizing said basal body temperature judged by said temperature measuring means together with a day of period of menstruation of the woman under checking,
 processing means for calculating data related to birth control based on the basal body temperature for a desired period memorized in the body temperature memory means, and to memorize it,
 display means for displaying the basal body temperature memorized in the body temperature memory means in the menstruation period unit and for indicating said data relating to birth control memorized in said processing means, and
 output means for sending out a print out signal for printing said basal body temperature and the data relating to birth control based o said basal body temperature by using a printer.

According to the women's clinical thermometer having the above construction, the temperature measuring means recognize the detected body temperature by an input signal from the body temperature detector, and after judging a fact that the detected body temperature has exceeded a predetermined temperature and that variation of the detected body temperature lies within a preset permissible temperature range, or a time lapsed from the start of measurement of the body temperature had exceeded a predetermined time, the highest detected temperature detected during the said predetermined period is judged as the basal body temperature. The body temperature memory means memorize the basal body temperature measured as above together with calendar date and the date of menstruation period. Further the indicating means display the basal body temperature memorized in the body temperature memory means by a unit of menstruation period and also indicate the data relating to birth control. The output means delivers a print out signal for the printer for recording and printing out the data related to the birth control based on the basal body temperature.

DETAILED EXPLANATION OF THE PREFERRED EMBODIMENT

The invention will now be explained by referring to the accompanying drawings.

Figure 1:
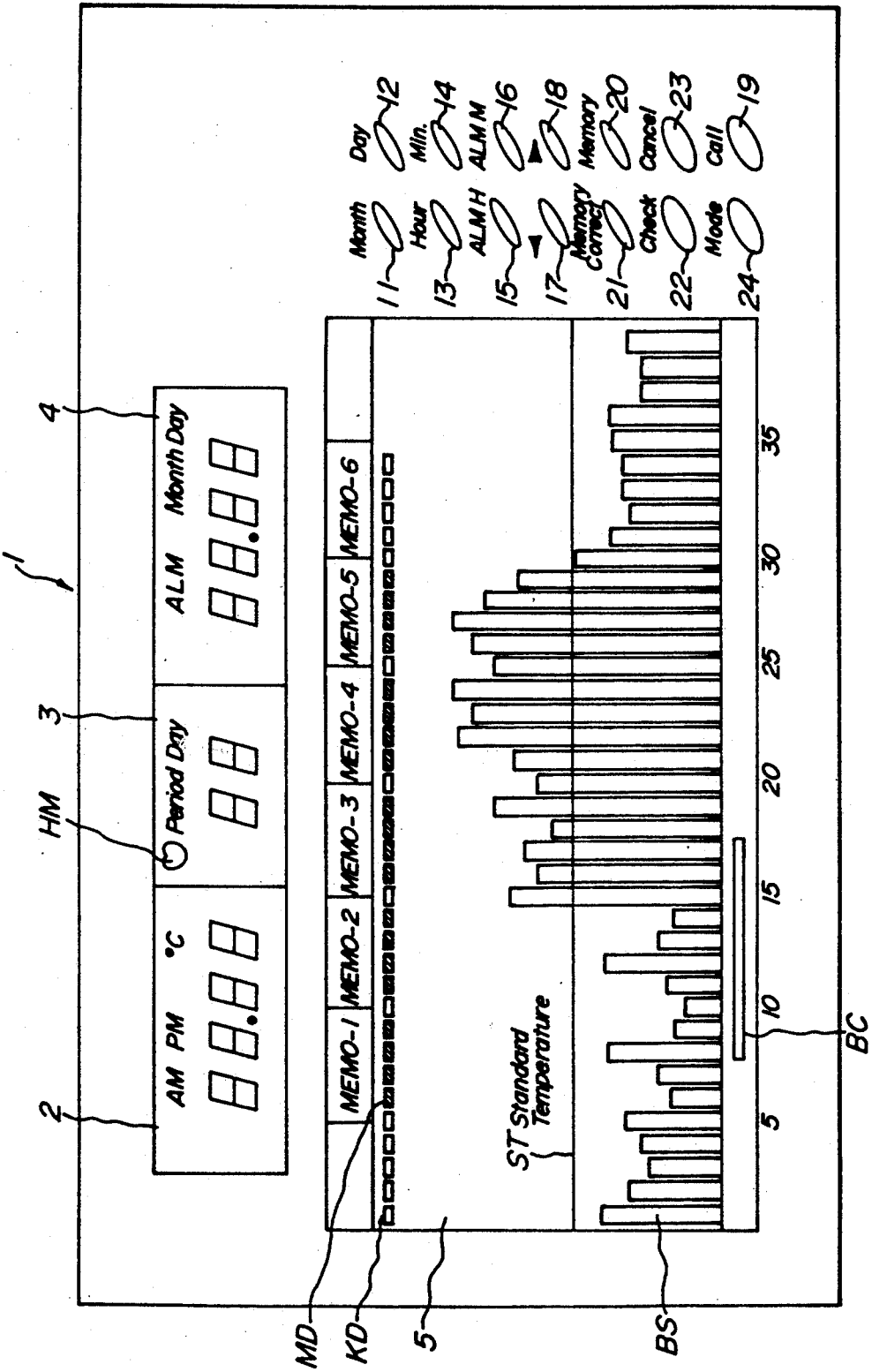
FIG. 1 shows a panel surface diagram of the women's clinical thermometer according to the present invention.

FIG. 1 shows plan view of the panel surface of women's clinical thermometer having an arrangement of various parts of the device according to the invention.

As can be seen from FIG. 1, on the panel surface of the women's thermometer 1 there is provided with a first indicator 2, formed of LCD (liquid crystal display), which indicates the real time in the normal indication condition with indication for AM and PM to indicate before noon or after noon. In the measuring condition of the device, this first indicator 2 acts to indicate the measured body temperature of a woman by numerals judged by a body temperature measuring algorithm which will be explained in detail hereinafter. Adjacent to this first indicator 2, there is provided with a second LCD indicator 3 including a heart mark HM which will be turned on when a pregnancy condition is judged to exist based on the basal body temperature which also will be explained later. This indicator 3 further includes an indication for the number of day in a menstruation period making the initial day of the menstruation period as the first day. Adjacent to this second indicator 3, there is a third indicator 4 which indicates in its ordinary indicating condition, the calendar month and calendar day of the day using the device and an alarm indication which operates at a preset alarm time to notify by an indication of characters "ALM" for a certain period. This portion operates to indicate the due date during turning on of said heart mark "HM" for indicating pregnancy condition and a switch 12, which will be explained later, is depressed. In said preset alarm time, a buzzer 38, which also will be explained later, operates to produce buzzer tone for a predetermined period so that the body temperature is to be measured within a term one hour before and after the buzzer tone and this temperature measuring data is memorized in a micro-computer which will be explained later.

The temperature measuring algorithm for determining the basal body temperature is as follows.

(1) The detected woman's body temperature measured by a body temperature detector 30 (refer to FIG. 2) had exceeded 35° C.

(2) After exceeding 35° C. of the detected woman's body temperature, the variation range of the detected temperature reached less than 0.02° C. within thirty second.

(3) In the above items (1) and (2), if the detected temperature falls down more than 0.2° C., a temperature measuring error is concluded.

Figure 2:
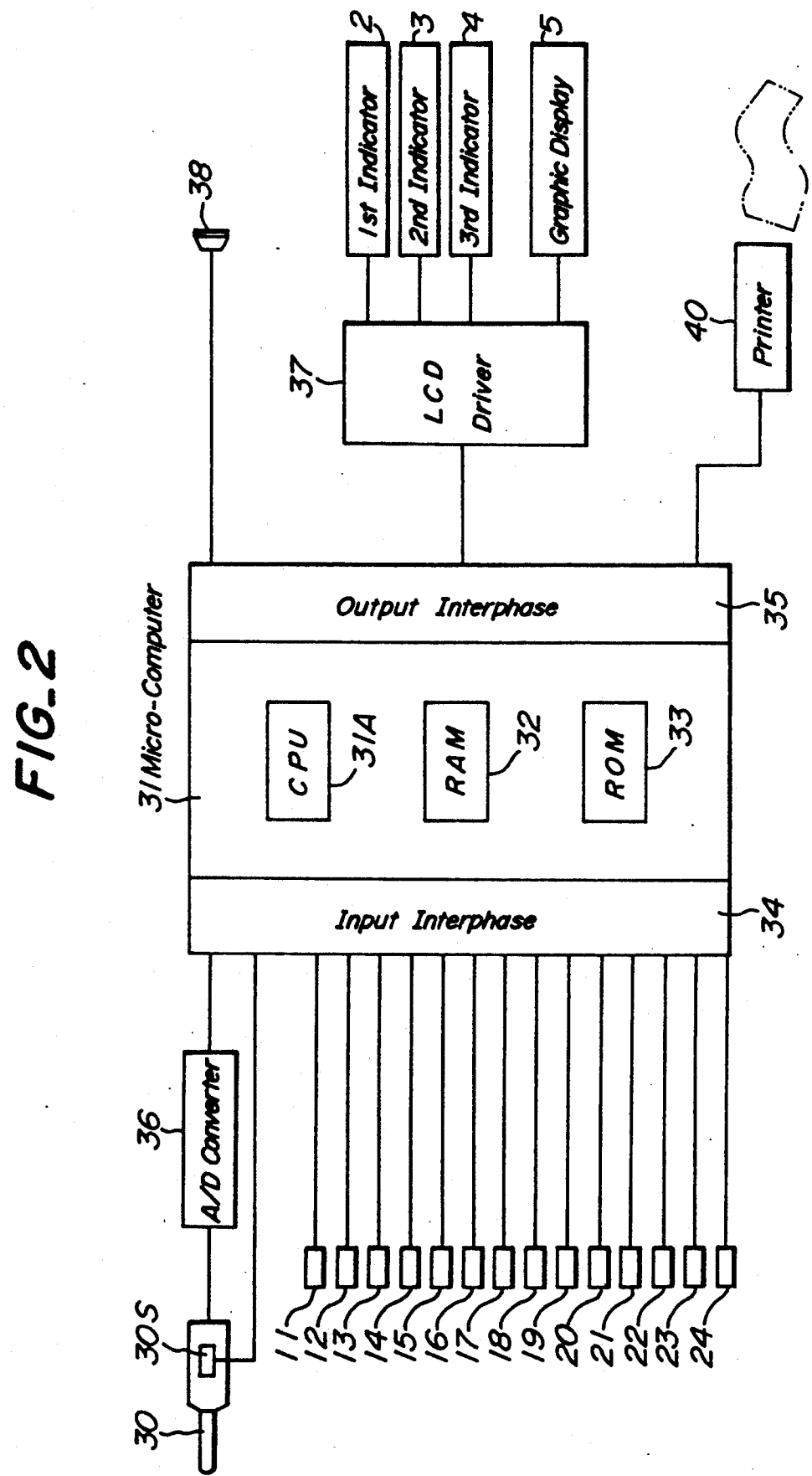
FIG. 2 shows a block diagram of an electronic circuit of the same women's thermometer.

(4) Both the above items (1) and (2) are satisfied, a buzzer 38 (refer to FIG. 2) is energized to produce signal tone to indicate completion of the temperature measurement and the highest temperature in the above item (2) is judged as the basal body temperature and this temperature is stored in the memory RAM (FIG. 2). However, if the above measurement completion time is less than five minutes, the temperature measurement is continued and the highest temperature after a lapse of five minutes from the starting of this temperature measurement is assumed as the basal body temperature. This value is stored in the memory RAM 32 and a completion signal tone different from the above temperature measurement completion tone is produced.

Underneath the above mentioned first indicator 2, the second indicator 3 and the third indicator 4, there is provided a graphic display 5 for indicating the basal body temperature BS of the woman in the form of a vertical bar graph measured for each successive day of the woman's menstruation period. The graphic display 5 also indicates by a horizontal line the standard temperature ST which is a mean value between the mean body temperature of the lower temperature period and the mean body temperature of higher body temperature period. This graphic display 5 has its indicating portion formed by LCD dots. Each indicating line for BS corresponds to each successive day of a menstruation period and extends in vertical direction and having, for instance, 27 dots, of which each dot corresponds to a 0.05° C. unit. At about middle of the vertically extending temperature indicating dots, there is one horizontal dot line for indicating the standard temperature ST. Further, under the temperature indicating dots for BS, there is a birth control period indicating dot BC extending in one horizontal line.

At the upper side of the body temperature indicating dots (BS), there are memo indicating dots MD, i.e. MEMO-1, MEMO-2, --- MEMO-6, arranged in one lateral row. These memo dots MEMO-1 to MEMO-6 are used to indicate memory items comprising important predetermined diagnostic information for the gynaecologist in the diagnosis and guidance for women relating, to control of conception. This information may include, for instance, bleeding condition, menorrhagia, discharge from the womb (hereinafter simplified by discharge), sexual intercourse, attack of fever, doping of drugs like ovulation promoter, etc. Such information can be memorized or stored in the thermometer 1 by operating corresponding keys or switches provided for each of the items. In order to individually indicate the above memo items of the above memo indicating dots MD, indicators for MEMO-1, MEMO-2, MEMO-3, MEMO-4, MEMO-5 and MEMO-6 are provided at the top outside of the graphic display 5 as shown in FIG. 1. The indicators may relate the following information;

MEMO-1—bleeding
MEMO-2—menorrhagia
MEMO-3—discharge
MEMO-4—intercourse
MEMO-5—fever
MEMO-6—doping At the right hand of the graphic display 5 there are arranged various controlling push button switches.

As can be seen from FIG. 1, said controlling push button switches are arranged in two columns each having six switches and altogether twelve switches. At the setting top of the columns, a switch 11 for setting the calendar "month" and a switch 12 for setting the calendar "day" are arranged. Below this row, a switch 13 for setting "hour" in the 24 hour indication and a switch 14 for setting "minute" are arranged. Further below this row, a switch 15 for setting "hour" of the alarm time for notifying a time to measure the body temperature to a person under supervision by alarm and a switch 16 for setting "minute" of the alarm time. Also a left shift switch 17 for shifting the measured body temperature displayed by the graph line BS on the graphic display 5 at each periodical day towards left and a right shift switch 18 to shift the display towards right at each day by day.

Furthermore, six control switches are arranged as shown in FIG. 1. These switches are as follows.

call switch—19
memory switch—20
memory correct switch—21
check switch—22
cancel switch—23
mode switch—24

A call switch 19 located at the extreme bottom right is used to call the measured temperature data memorized in the RAM 32 of a micro-computer 31 which will be explained hereinafter for a week unit by each file by file beginning from the newest file and to indicate the content of the file by the line graph BS on the graphic display 5 so as to place in "call condition". By once depressing this call switch 19, the body temperature measuring data under proceeding is called out to display it by the line graph BS. This data is displayed by making the left end line graph BS as the initial day of the menstruation and the lines towards the right direction indicate the more recent days of the cycle. When depressing the call switch 19 once more, a temperature measuring data of the previous file is indicated.

There is also a memory switch 20 as shown in the drawing. When this memory switch 20 is depressed, the date indicated on the third indicator portion 4 in the ordinary indicating condition is registered in the RAM 32 as the most recent initial day of the menstruation and the graphic display 5 becomes said call condition. However, if this date is not passed over 10 days counted from the initial day of the previous menstruation period, such date is not registered as the new initial date of the menstruation period.

When the memory correction switch 21 is depressed, the indicated date showing the first day of the most recent menstruation period on the third indicator 4 registered by said memory switch 20 will start to turn on and off. At the same time, the indicating portion for the temperature of the first indicator 2 and that for the day of a certain menstruation period of the second indicator 3 become blank and the graphic display 5 also becomes blank. At this condition, the first date of the menstruation period can be changed to the date desired by using the switches 11 and 12 and referring to the third indicator 4. After setting the desired date, the memory correction switch 21 may be depressed. Then the turning on and off of the date indication on the third indicator 4 is discontinued and this date is registered as the corrected initial date of the newly corrected term.

The check switch 22 acts as follows. When this check switch 22 is depressed in said call condition, temperature indicting dot BS on the extreme left side of the graphic display 5 starts to turn on and off at a period of 0.4 sec±0.1 sec for a duration of 5 sec±0.5 sec and corresponding data, i.e. temperature, day of the period, and the first day of the menstruation period are indicated on the first indicator 2, second indicator 3, and fourth indicator 5, respectively. With the turning on and off of the extreme left dot BS on the graphic display 5, the next dot on the right will start and turn on and off to indicate the same data as above to proceed to show successive indication until the extreme right end and the temperature, day of period and the first day of the menstruation period are alas indicated.

The cancel switch 23 acts to stop all the processes then undergoing and to restore to the ordinary indicating condition, when it is depressed. Also it acts to delete the most recently registered body temperature measuring data among the memorized data in RAM 32. However, this deletion is limited to a condition that the device is in the ordinary indicating condition, that the time lapsed from the most recent body temperature measurement is not exceeding more than 5 minutes±15 seconds, and that the body temperature measuring data is the first measurement within one hour before and after of said alarm time. Furthermore, an erroneously registered memory of the first date of a menstruation period can be cancelled as far as the registered memory data is under a correction condition.

The mode switch 24 acts to secure the operation of other switches 11-23 when it is depressed simultaneously with one of said other switches to make the operation of other switches definite. In other words, to eliminate an erroneous operation of said other switches when contacted unintentionally and to secure the result of operation definitely only when these switches are operated by backing up the controlling signal.

The thermometer 30 shown in FIG. 2 and used for measuring the body temperature of a person to be supervised has a temperature measuring switch 30S, which is to be depressed at the time to start the measurement.

Now, an electronic circuit block diagram shown in FIG. 2 will be explained.

As shown in FIG. 2, as a most essential part of the electronic circuit of the women's thermometer a micro-computer 31 is provided. This micro-computer 31 comprises a central processing unit (CPU) 31A, said RAM 32, a ROM 33 accommodating various processing programs, an input interphase 34, and an output interphase 35.

To the above mentioned input interface 34, the various switches explained above are connected. Also a temperature detector 30 used in the measurement of body temperature of a woman is coupled via an A/D converter 36. To this A/D converter and to the input interphase, the above mentioned temperature measuring switch 30S is connected, which is associated with and accommodated in the base of the temperature detector 30.

Connected to the output interphase 35, is an LCD driver circuit 37 for driving said first indicator 2, second indicator 3, third indicator 4 and the graphic display 5, respectively. Also a buzzer 38 to produce a buzzer tone at the alarm time or at the operation time of said switches 11-24 is connected to the output interphase 35.

The output interphase 35 comprises a printer connecting interphase for connecting printer 40 for typing out various input data to the microcomputer 31 and stored in it.

As for the data to be printed out by the printer 40 there are basal body temperature of maximum six periods and the measured date, first date of the menstruation period, ovulation day, date of birth control, said memo items, data for pregnancy, etc.

The function of the device 1 to judge pregnancy based on the basal body temperature, to turn on said heart mark HM, to calculate the due date based on the ovulation day and to display such data, will now be explained.

Based on the measured basal body temperature, after the low temperature period when there is more than 21 days of high temperature period, the micro-computer 31 judges that there is pregnancy condition and turns on the heart mark HM from the 21st day until first day of the next menstruation period.

The micro-computer 31 decides the ovulation day based on the following condition.

(1) More than 7 days have lapsed from the first day of menstruation.

(2) The body temperature measured on the day is higher than the standard temperature ST, and the measured body temperature is higher than the lowest body temperature in the menstruation period by 0.3° C. for 3 consecutive days including the same day.

If both of the above two conditions are fulfilled, 4th days counted before this day is assumed as the ovulation day and memorized in the RAM 32.

Then by taking the ovulation day decided in the above process as the first day, a calculated 266th day is deemed as the due date and it is memorized in the RAM 32. Under the condition that the heart mark HM is turned on, when said day switch 12 is depressed, the above due date is indicted on said third indicator 4.

According to the present invention, the basal body temperature can be measured accurately by the temperature measuring algorithm in the temperature measuring means. Also the basal body temperature measured and memorized for a desired period and the birth control data calculated by said basal body temperature can be printed out altogether when desired and it can be displayed or recorded by digital value or graphic display. Accordingly, by monitoring her body temperature using the device a woman can immediately recognize the change of basal body temperature of herself and the birth control data. The gynaecologist can provide exact diagnosis or advice based on the displayed data relating to the birth control.

What is claimed is:

1. A clinical thermometer for women comprising in combination:
   a microprocessor including calendar means for refreshing stored date data at the lapse of each 24 hours based on real time and for outputting such real time date data of month, day and time to related portions of the thermometer;
   detecting means connected to said microprocessor for detecting basal body temperature of a woman user;
   body temperature memory means for storing the detected body temperature together with the output date data of said calendar means,
   display means for graphically displaying the stored basal body temperature together with the output date data of said calendar means;
   memo item input means for receiving medical data of the woman user with respect to her conception and for inputting such medical data for use in the diagnosis of her conception;
   memo item memory means for memorizing respective data input from the memory item input means at its occurrence together with the output data of the calendar means, and
   memo item display means for indicating data corresponding to the respective occurred items stored in the memo item memory means together with the output data of the calendar means, and for displaying said memo item data together with the output of the calendar means.

2. The clinical thermometer for women described in claim 1 including in combination,
   printing means for printing out said basal body temperature memorized in said body temperature memory means together with the data relating to the memo items and the output data of the calendar means.

3. A clinical thermometer for women as described in claim 1 or 2, wherein the predetermined memo items are bleeding, menorrhagia, discharge, intercourse, fever, and doping such as an ovulation stimulator.

4. A clinical thermometer for women as described in claim 1,
   wherein the thermometer further comprises;
   initial day of menstruation input means for providing an input representing the initial day of the menstruation of the user woman at each menstruation period,
   initial day of menstruation memory means for storing the initial day of menstruation input information from said initial day of menstruation memory means together with the output data of said calendar means,
   standard body temperature calculation means for calculating standard body temperature of the user based on said basal body temperature stored in said body temperature memory means together with the output data of said calendar means, the standard body temperature being an average temperature of an average basal body temperature in a low temperature period and in a high temperature period of the present menstruation period of the user woman,
   first logic means in said microprocessor for detecting a situation of several continuous days of high body temperature that is higher than said standard body temperature calculated by said standard body temperature calculation means and higher than the lowest temperature of a relevant menstruation period over a predetermined number of days including the same day,
   second logic means for detecting the lapse of a predetermined number of days counted from the initial day of the present menstruation period,
   ovulation day judging means for judging as the ovulation day when both the first and second logic means judge the predetermined condition and that a predetermined number of days from the present day is an ovulation day,
   pregnancy judging means for judging the pregnancy condition of the user woman after judging the ovulation day by said ovulation day judging means and furthermore after the low temperature period of the present menstruation period of the woman occurrence of more than a predetermined number of days of high temperature period of the present menstruation period as being a pregnancy condition of the user woman, and
   a pregnancy condition indicating means for indicating the pregnancy condition when the pregnancy condition is judged by said pregnancy judging means.

5. A clinical thermometer for women comprising in combination,
   a microprocessor including calendar means for refreshing stored date data at the lapse of each 24 hours based on real time and for outputting such real time date data for month, day and time to related portions of the thermometer;
   detecting means connected to said microprocessor for detecting basal body temperature of a woman;
   body temperature memory means for storing the detected body temperature together with the output date data of said calendar means, display means for graphically displaying stored basal body temperature together with the output date data of said calendar means;

memo item input means for receiving medical data of the woman with respect to her conception and for inputting such medical data for use in the diagnosis of her conception;

memo item memory means for memorizing respective data input from the memo item input means at its occurrence together with the output data of the calendar means, and memo item display means for indicating data corresponding to the respective occurred items stored in the memo item memory means together with the output data of the calendar means, and for displaying said memo item data together with the output of the calendar means;

wherein the thermometer further comprises;

initial day of menstruation input means for providing an input representing the initial day of the menstruation of said woman at each of menstruation period, initial day of menstruation memory means for storing the initial day of menstruation information provided by said initial day of menstruation input means together with the output data of said calendar means, standard body temperature calculation means for calculating standard body temperature based on said basal body temperature stored in the body temperature memory means together with the output data of the calendar means, the standard body temperature being an average temperature of an average basal body temperature in a low temperature period and that in a high temperature period of the present menstruation period of the user woman, first logic means in said microprocessor for detecting a situation of several continuous days of high body temperature that is higher than said standard body temperature calculated by said standard body temperature calculation means and higher than the lowest temperature of a relevant menstruation period over a predetermined number of days including the same day, second logic means for detecting the lapse of a predetermined number of days counted from the initial day of the present menstruation period, ovulation day judging means for judging as the ovulation day when both the first and second logic means indicate the predetermined condition and that a predetermined number of days from the present day is an ovulation day, pregnancy judging means for judging the pregnancy condition of the user woman after judging the ovulation day by said ovulation day judging means and furthermore after the low temperature period of the present menstruation period of the woman occurrence of more than a predetermined number of days of high temperature period of the present menstruation period as being a pregnancy condition of the woman, a pregnancy condition indicating means for indicating the pregnancy condition when the pregnancy condition is judged by said pregnancy judging means, due date calculating means for calculating the due date when the pregnancy condition is judged by the pregnancy condition judging means by counting a predetermined number of days from the ovulation day judged by said ovulation day judging means as the first day, and due date indicating means for indicating the due date calculated by said due date calculating means.

6. A clinical thermometer for women as described in claim 5 comprising in combination, printing means for printing out the data concerning pregnancy condition when said user woman is judged to be in a pregnancy condition by the pregnancy condition judging means together with the due date calculated by said due date calculating means.

7. A clinical thermometer for women as described in claim 5 or 6, wherein in the due date calculating means for calculating the due date takes the ovulation day judged by said ovulation day judging means as the first day and 226th day thereafter as being the due date.

8. A clinical thermometer for women comprising in combination, a microprocessor including calendar means for refreshing stored date data at the lapse of each 24 hours based on real time and for outputting such real time date data for month, day and time to related portions of the thermometer, detecting means connected to said microprocessor for detecting basal body temperature of a woman;

body temperature memory means for storing the detected body temperature together with the output date data of said calendar means, display means for graphically displaying stored basal body temperature together with the output date data of said calendar means;

initial day of menstruation input means for providing an input representing the initial day of the menstruation of said woman at each of menstruation period, initial day of menstruation memory means for storing the initial day of menstruation information provided by said initial day of menstruation input means together with the output data of the calendar means, standard body temperature calculation means for calculating standard body temperature based on said basal body temperature memorized in the body temperature memory means together with the output data of the calendar means, the standard body temperature being an average temperature of an average basal body temperature in a low temperature period and that in a high temperature period of the present menstruation period of the user woman, first logic means for detecting a situation of several continuous days of high body temperature that is higher than said standard body temperature calculated by said standard body temperature calculation means and higher than the lowest temperature of a relevant menstruation period over a predetermined number of days including the same day, second logic means for detecting the lapse of a predetermined number of days counted from the initial day of present menstruation period, ovulation day judging means for judging as the ovulation day when both the first and second logic means have detected the predetermined condition and that a predetermined number of days from the present day is an ovulation day, birth control term setting means for setting as a birth control period taking the ovulation day determined by said ovulation day judging means and the period bridging predetermined days prior and after the ovulation day, and birth control term indicating means on said thermometer for indicating said birth control term as set by said birth control term setting means.

9. A clinical thermometer for women as described in claim 8 comprising in combination, printing means for printing out said birth control term.

* * * * *